(12) United States Patent
Matlock et al.

(10) Patent No.: US 11,686,043 B2
(45) Date of Patent: Jun. 27, 2023

(54) PULL WIRE WITH COATED FIBERS

(71) Applicant: ACCLARENT, INC., Irvine, CA (US)

(72) Inventors: George L. Matlock, Pleasanton, CA (US); John H. Thinnes, Jr., Mission Viejo, CA (US)

(73) Assignee: Acclarent, Inc., Irvine, CA (US)

(*) Notice: Subject to any disclaimer, the term of this patent is extended or adjusted under 35 U.S.C. 154(b) by 842 days.

(21) Appl. No.: 16/590,707

(22) Filed: Oct. 2, 2019

(65) Prior Publication Data
US 2020/0139082 A1 May 7, 2020

Related U.S. Application Data

(60) Provisional application No. 62/755,684, filed on Nov. 5, 2018.

(51) Int. Cl.
| D07B 3/02 | (2006.01) |
| A61M 25/01 | (2006.01) |
| A61M 29/00 | (2006.01) |
| A61M 25/00 | (2006.01) |
| A61B 17/24 | (2006.01) |
| A61M 29/02 | (2006.01) |

(52) U.S. Cl.
CPC .......... *D07B 3/02* (2013.01); *A61B 17/24* (2013.01); *A61M 25/0009* (2013.01); *A61M 25/0147* (2013.01); *A61M 29/00* (2013.01); *A61M 2029/025* (2013.01); *A61M 2205/0238* (2013.01); *D07B 2201/2087* (2013.01); *D07B 2205/205* (2013.01); *D07B 2207/404* (2013.01)

(58) Field of Classification Search
CPC ............. D07B 3/02; D07B 7/14; D07B 7/145

USPC ............................................. 57/7, 11, 12, 59
See application file for complete search history.

(56) References Cited

U.S. PATENT DOCUMENTS

| 874,287 A | * | 12/1907 | Bayne et al. ...... | B29D 30/0633 |
| | | | | 118/420 |
| 1,071,676 A | * | 8/1913 | Heany ...................... | D02G 3/36 |
| | | | | 43/18.5 |

(Continued)

FOREIGN PATENT DOCUMENTS

| CN | 1986958 B | 6/2010 |
| JP | H05-163688 A | 6/1993 |

(Continued)

OTHER PUBLICATIONS

International Search Report and Written Opinion dated Jan. 28, 2020 for International Application No. PCT/IB2019/059452, 14 pages.

*Primary Examiner* — Shaun R Hurley
(74) *Attorney, Agent, or Firm* — Frost Brown Todd LLP

(57) ABSTRACT

A method is provided for making a fiber wire having a fiber bundle core and a polymer jacket. The method includes rotating a spool of fiber bundle about a first rotational axis to progressively unwind the fiber bundle from the spool. The fiber bundle includes a plurality of continuous synthetic fiber filaments. While the spool is rotated about the first rotational axis, the spool is simultaneously rotated about a second rotational axis to thereby twist the unwound fiber bundle about its longitudinal axis. The method further includes coating the twisted fiber bundle with a molten polymer, and permitting the molten polymer to cool to define a flexible outer jacket that encapsulates the twisted fiber bundle.

20 Claims, 10 Drawing Sheets

(56) References Cited

U.S. PATENT DOCUMENTS

| | | | |
|---|---|---|---|
| 1,797,249 A * | 3/1931 | Simpson | D07B 3/06 |
| | | | 57/295 |
| 1,990,071 A | 2/1935 | Green et al. | |
| 3,243,948 A | 4/1966 | Flanigan | |
| 4,156,624 A * | 5/1979 | de Vecchis | G02B 6/4491 |
| | | | 156/244.15 |
| 4,607,481 A * | 8/1986 | Bell | D02G 3/36 |
| | | | 57/7 |
| 4,677,818 A | 7/1987 | Honda et al. | |
| 5,060,466 A * | 10/1991 | Matsuda | D07B 1/025 |
| | | | 57/232 |
| 5,360,482 A * | 11/1994 | Belvedere | B05C 3/132 |
| | | | 401/9 |
| 6,090,319 A * | 7/2000 | Sharma | B29B 9/14 |
| | | | 264/108 |
| 6,186,769 B1 | 2/2001 | Hawley | |
| 9,155,492 B2 | 10/2015 | Jenkins et al. | |
| 10,610,308 B2 | 4/2020 | Sema et al. | |
| 2010/0122625 A1* | 5/2010 | Wang | A63B 21/0552 |
| | | | 87/2 |
| 2010/0224309 A1 | 9/2010 | Tashiro et al. | |
| 2010/0242253 A1* | 9/2010 | Schwartz | D02G 3/286 |
| | | | 139/11 |
| 2010/0274188 A1 | 10/2010 | Chang et al. | |
| 2011/0004057 A1 | 1/2011 | Goldfarb et al. | |
| 2011/0173873 A1* | 7/2011 | Nakanishi | D02G 3/44 |
| | | | 43/44.98 |
| 2012/0000174 A1* | 1/2012 | Pottier | D07B 1/0633 |
| | | | 57/7 |
| 2012/0240547 A1* | 9/2012 | Onnis | D02G 3/444 |
| | | | 57/210 |
| 2012/0277768 A1 | 11/2012 | Viola et al. | |
| 2013/0274715 A1 | 10/2013 | Chan et al. | |
| 2014/0221920 A1 | 8/2014 | Jimenez | |
| 2016/0008083 A1 | 1/2016 | Kesten et al. | |
| 2018/0064481 A1 | 3/2018 | Coulombe et al. | |
| 2018/0078737 A1 | 3/2018 | Gonzalez | |
| 2018/0311472 A1 | 11/2018 | Matlock et al. | |
| 2019/0015645 A1 | 1/2019 | Matlock et al. | |
| 2019/0015646 A1 | 1/2019 | Matlock et al. | |
| 2019/0192177 A1 | 6/2019 | Palushi et al. | |

FOREIGN PATENT DOCUMENTS

| | | |
|---|---|---|
| JP | 2002-266266 A | 9/2002 |
| WO | WO 2000/067834 A1 | 11/2000 |
| WO | WO 2018/022418 A2 | 2/2018 |

* cited by examiner

US 11,686,043 B2

PULL WIRE WITH COATED FIBERS

PRIORITY

This application claims the benefit of U.S. Provisional Pat. App. No. 62/755,684, entitled "Pull Wire with Coated Fibers," filed Nov. 5, 2018, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, now abandoned, the disclosure of which is incorporated by reference herein; and U.S. Patent Pub. No. 2013/0274715, entitled "Method and System for Eustachian Tube Dilation," published on Oct. 17, 2013, now abandoned, the disclosure of which is incorporated by reference herein. An example of such a system is the Aera® Eustachian Tube Balloon Dilation System by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry® Sinus Illumination System by Acclarent, Inc. of Irvine, Calif.

It may be desirable to provide easily controlled placement of a balloon of a dilation catheter in an anatomical passageway, including in procedures that will be performed only by a single operator. While several systems and methods have been made and used to position a balloon of a dilation catheter in an anatomical passageway, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1A:
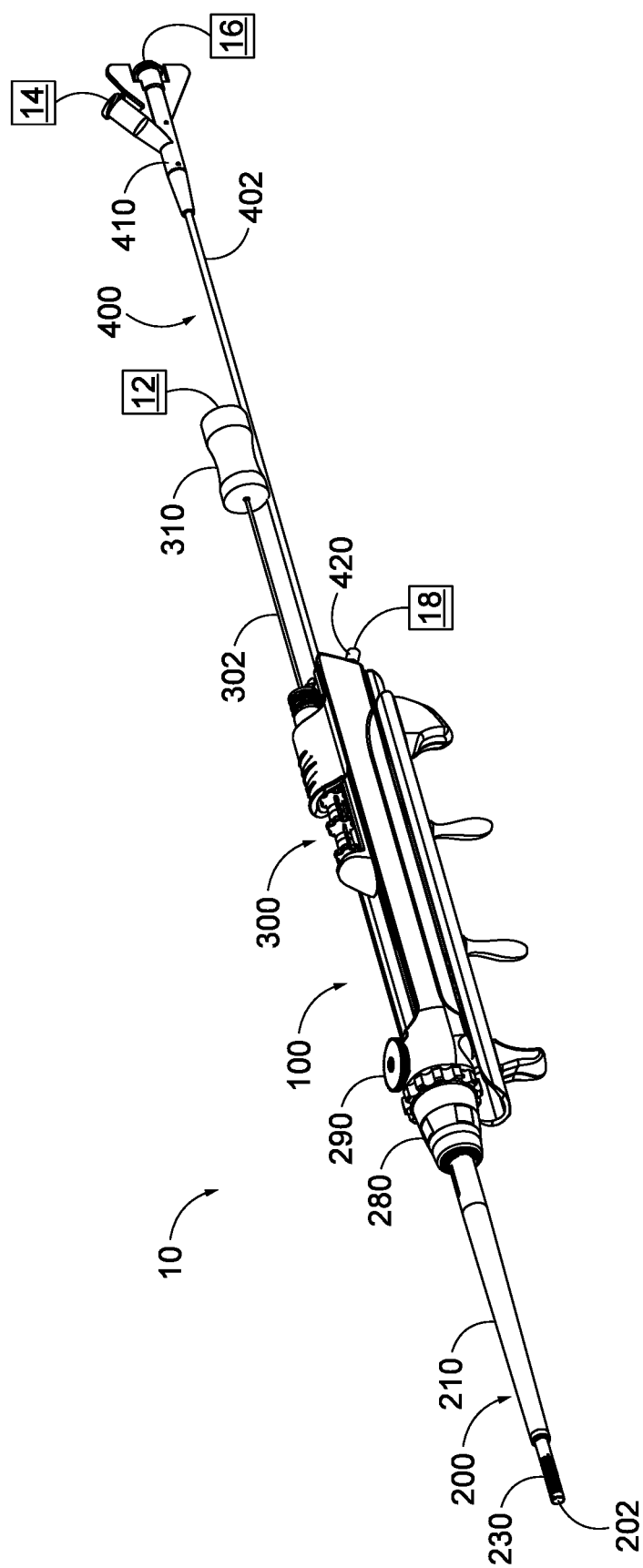
FIG. 1A depicts a perspective view of an exemplary dilation instrument, with a guidewire and a dilation catheter each in respective proximal positions.
Figure 1B:
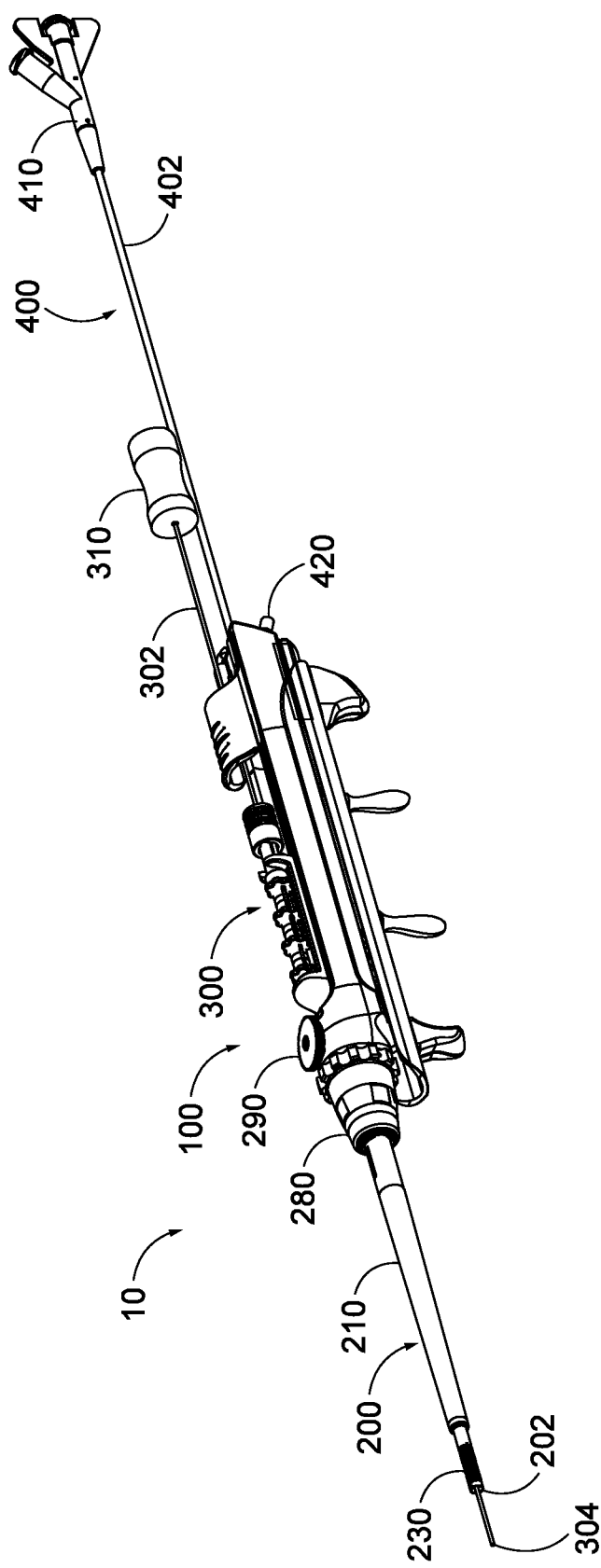
FIG. 1B depicts a perspective view of the instrument of FIG. 1A, with the guidewire in a distal position and the dilation catheter in the proximal position.
Figure 1C:
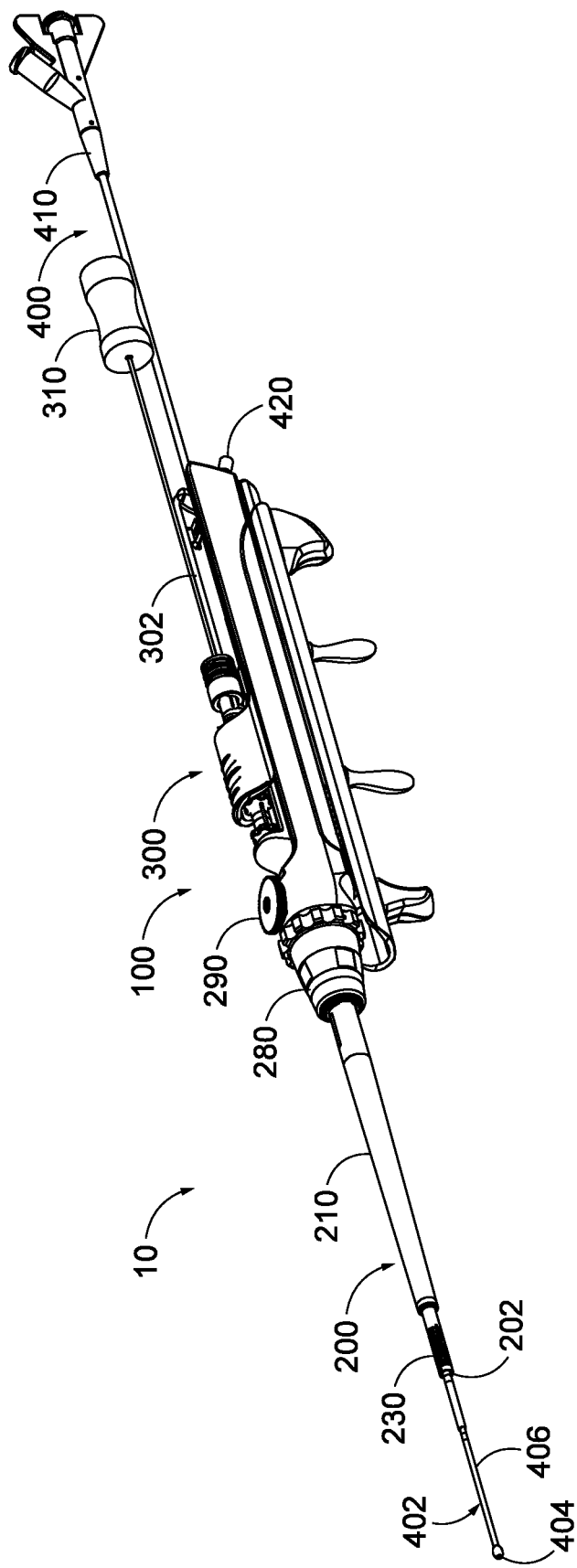
FIG. 1C depicts a perspective view of the instrument of FIG. 1A, with the guidewire and the dilation catheter each in respective distal positions, and with a dilator of the dilation catheter in a non-expanded state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY DILATION INSTRUMENT

A. Overview

FIGS. 1A-1D show an exemplary dilation instrument (10) that may be used to dilate an ostium or other passageway associated with drainage of a paranasal sinus, a Eustachian tube, or some other anatomical passageway (e.g., within the ear, nose, or throat, etc.). As will be described in greater detail below, dilation instrument (10) of the present example provides adjustability that enables the operator to use dilation instrument (10) in different scenarios, without requiring the operator to switch between different instruments. For instance, dilation instrument (10) may be used to dilate various different anatomical passageways (e.g., frontal sinus ostium, frontal recess, maxillary sinus ostium, sphenoid sinus ostium, ethmoid sinus ostium, Eustachian tube, etc.) by making simple adjustments to structural features of the instrument.

Dilation instrument (10) of this example includes a handle assembly (100), a guide shaft assembly (200) extending distally from handle assembly (100); a guidewire actuation assembly (300) slidably coupled with handle assembly (100); and a dilation catheter actuation assembly (400) slidably coupled with handle assembly (100). A guidewire module (12) is coupled with a guidewire (302) of instrument (10) via a connector (310). An inflation fluid source (14) and an irrigation fluid source (16) are fluidly coupled with a dilation catheter (402) of instrument (10) via a connector (410). A suction source (18) is coupled with a suction port (420) of instrument (100).

Figure 1D:
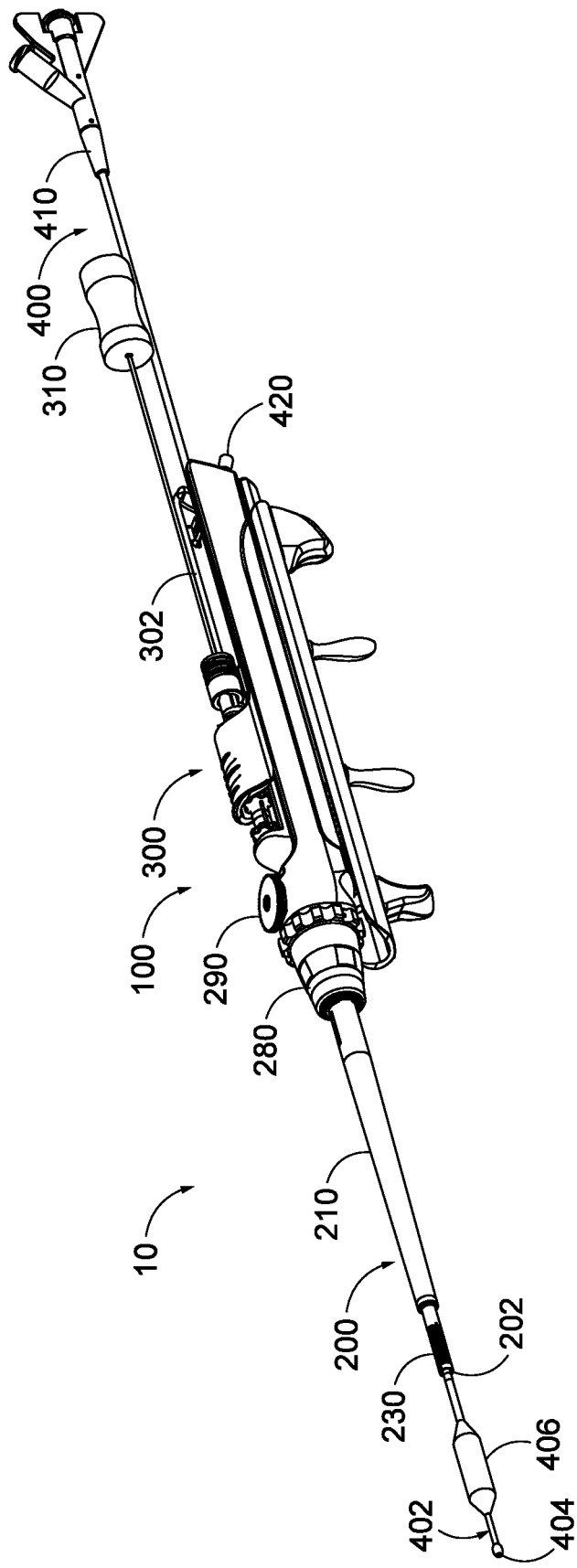
FIG. 1D depicts a perspective view of the instrument of FIG. 1A, with the guidewire and the dilation catheter each in respective distal positions, and with a dilator of the dilation catheter in an expanded state.

Handle assembly (100) is sized and configured to be grasped and operated by a single hand of an operator. The operator may selectively operate guidewire actuation assembly (300) and dilation catheter actuation assembly (400) with the same single hand that grasps handle assembly (100). As shown in the transition from FIG. 1A to FIG. 1B, the operator may advance guidewire actuation assembly (300) distally along handle assembly (100) to thereby advance guidewire (302) distally, such that a distal end (304) of guidewire (302) is positioned distal to the distal end of guide shaft assembly (200). As shown in the transition from FIG. 1B to FIG. 1C, the operator may then advance dilation catheter actuation assembly (400) distally along handle assembly (100) to thereby advance a dilation catheter (402) distally along guidewire (302), such that the distal tip (404) of dilation catheter (402) is positioned distal to the distal end of guide shaft assembly (200). With dilation catheter (402) advanced to a distal position, the operator may then inflate a dilator (406) of dilation catheter (402) to achieve an expanded state as shown in FIG. 1D, to thereby dilate an anatomical passageway in which dilator (406) is positioned. In the present example, dilation catheter (402) is coaxially disposed within guide shaft assembly (200), and guidewire (302) is coaxially disposed within dilation catheter (402). In other examples, guide shaft assembly (200) may be coaxially disposed within dilation catheter (402), and guidewire (302) may be coaxially disposed within guide shaft assembly (200).

In some versions of dilation instrument (10), guidewire (302) may include one or more optical fibers, and distal end (304) may be configured to emit visible light. In some such versions, guidewire module (12) includes a light source, and connector (310) is operable to communicate light from the light source of guidewire module (12) to guidewire (302). Illuminating versions of guidewire (302) may be used to provide position confirmation through observation of transillumination effects. By way of example only, illuminating versions of guidewire (302) may be constructed and operable in accordance with at least some of the teachings of U.S. Pat. No. 9,155,492, entitled "Sinus Illumination Lightwire Device," issued Oct. 13, 2015, the disclosure of which is incorporated by reference herein.

In addition to providing illumination, or as an alternative to providing illumination, guidewire (302) may provide position sensing capabilities. In some such versions, the distal end of guidewire (302) may include a position sensor. By way of example only, such a guidewire (302) may be constructed and operable in accordance with at least some of the teachings of U.S. patent application Ser. No. 15/861,959, entitled "Navigation Guidewire with Interlocked Coils," filed Jan. 4, 2018, issued as U.S. Pat. No. 10,610,308 on Apr. 7, 2020; U.S. patent application Ser. No. 15/852,530, entitled "Reusable Navigation Guidewire," filed Dec. 22, 2017, now abandoned; and/or U.S. Pub. No. 2016/0008083, entitled "Guidewire Navigation for Sinuplasty," published Jan. 14, 2016, issued as U.S. Pat. No. 10,463,242 on Nov. 5, 2019, the disclosures of each of these references being incorporated by reference herein. In some such versions, guidewire module (12) includes an image-guided surgery (IGS) navigation system, and connector (310) is operable to communicate position-indicative signals from the position sensor of guidewire (302) to guidewire module (12). In other versions of dilation instrument (10), guidewire (302) may be omitted entirely.

B. Exemplary Guide Shaft Assembly and Associated Actuation Assemblies

Figure 2:
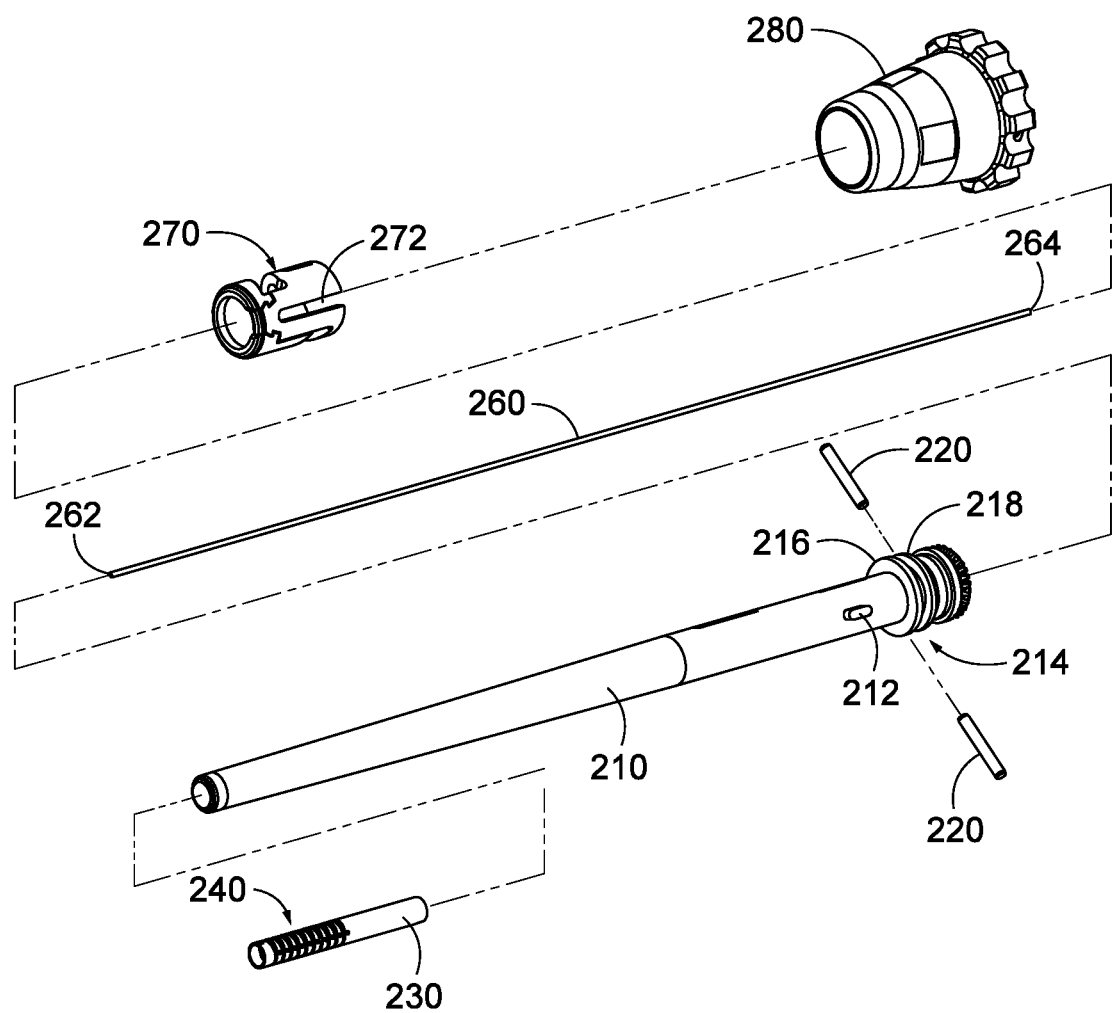
FIG. 2 depicts an exploded perspective view of a guide shaft assembly of the instrument of FIG. 1A.

As shown in FIGS. 2-3, guide shaft assembly (200) of the present example includes a rigid shaft member (210), a flexible shaft member (230) arranged at the distal end of rigid shaft member (210), a push-pull wire (260), a cam barrel (270), and a deflection control knob (280). Shaft members (210, 230), cam barrel (270), and deflection control knob (280) are coaxially aligned with each other in this example, with push-pull wire (260) being laterally offset from the central longitudinal axis shared by shaft members (210, 230), cam barrel (270), and deflection control knob (280). Shaft assembly (200) is operable to guide guidewire (302) and dilation catheter (402) along an operator-selected exit angle relative to the central longitudinal axis of guide shaft assembly (200).

Figure 3A:
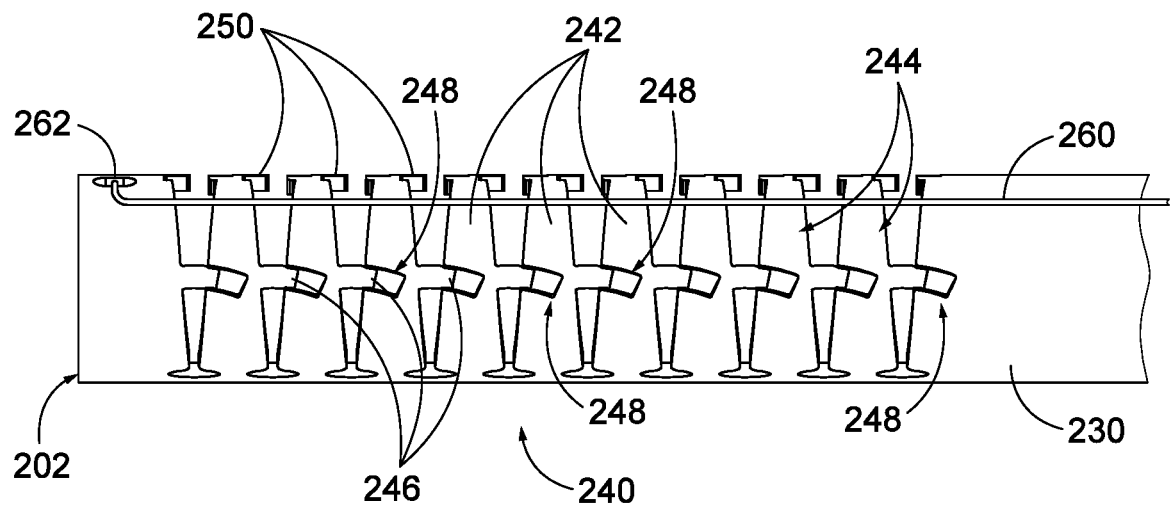
FIG. 3A depicts a cross-sectional side view of a distal portion of a flexible shaft member of the guide shaft assembly of FIG. 2, with the distal portion in a straight configuration.
Figure 3B:
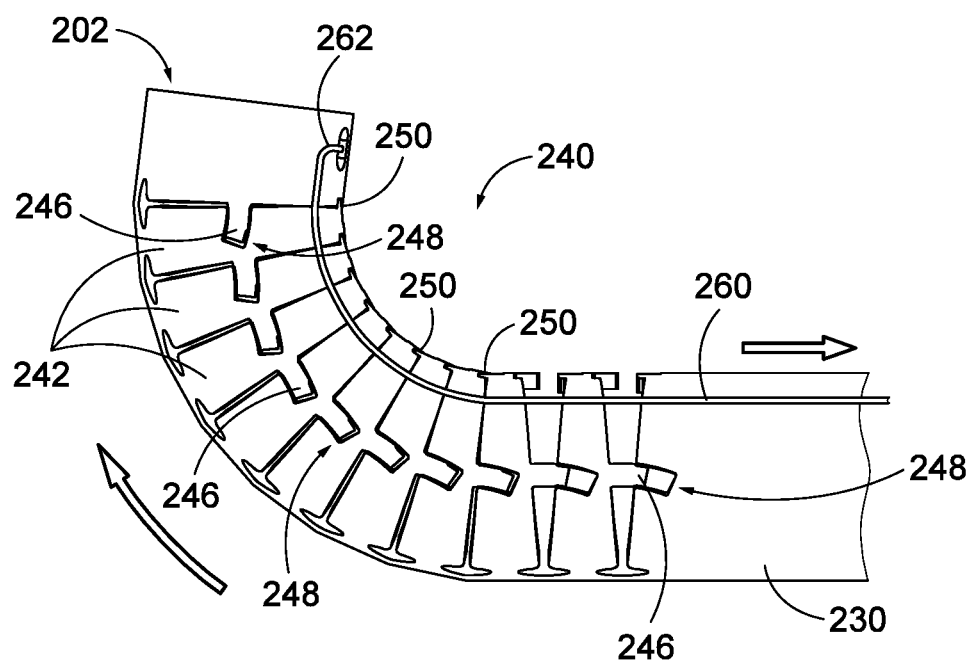
FIG. 3B depicts a cross-sectional side view of the flexible shaft member of FIG. 3A in a deflected configuration.

In some versions, both shall members (210, 230) are formed of a metallic material, such as stainless steel and/or nitinol. In some such versions, shaft members (210, 230) (and at least some other portions of instrument (10)) may be reusable, with such reusable components being subject to cleaning and sterilization between uses on different patients. In some other versions, one or both of shaft members (210, 230) may be formed of a polymeric material. In some such versions, shaft members (210, 230) may be treated as single-use-only components. Flexible shaft member (230) is secured to rigid shaft member (210) and is positioned distally in relation to rigid shaft member (210). As best seen in FIGS. 3A-3B, flexible shaft member (230) includes a flex section (240) that is formed by a series of ribs (242), which are separated by a series of notches (244). Notches (244) are generally V-shaped, with a circular opening at the vertex of each "V." Notches (244) also include tab portions (246) that fit in corresponding sub-notches (248). The top of each "V" includes a set of stop features (250).

As shown in FIG. 3A, when flex section (240) is in a straight configuration, tab portions (246) are disposed in corresponding sub-notches (248) but are not fully seated in sub-notches (248). As also shown in FIG. 3A, when flex section (240) is in a straight configuration, stop features (250) are separated from each other. FIG. 3B shows flex section (240) in a fully deflected (or "bent") configuration. In this state, tab portions (246) are fully seated in sub-notches (248) and stop features (250) are engaged with each other. During the transition between the states shown in FIGS. 3A-3B, tab portions (246) and sub-notches (248) may cooperate to ensure that flex section (240) deflects (or "bends") in a consistent fashion, with sufficient lateral stability; and that flex section (240) provides a consistent and stable deflected or straight state.

By way of example only, flex section (240) may be formed through laser cutting or any other suitable manufacturing process. In some versions, flex section (240) is covered with a flexible wrap (not shown). Such a flexible wrap may prevent tissue and other structures from getting snagged or pinched in notches (244), without compromising the flexibility of flex section (240). A flexible wrap may also ensure that suction provided through guide shaft assembly (200) is focused at a distal end (202) thereof. Various suitable forms that flex section (240) may take will be apparent to those of ordinary skill in the art in view of the teachings herein. By way of further example only, flex section (240) may be constructed and operable in accordance with at least some of the teachings of U.S. patent application Ser. No. 15/955,232, entitled "Deflectable Guide for Medical Instrument," filed Apr. 17, 2018, issued as U.S. Pat. No. 11,376,401 on Jul. 5, 2022, the disclosure of which is incorporated by reference herein.

Push-pull wire (260) is disposed within shaft members (210, 230) and is operable to provide controlled deflection (or "bending") of flex section (240). As shown in FIGS. 3A-3B, a distal end (262) of push-pull wire (260) is secured to the distal end (232) of flexible shaft member (230), distal to flex section (240). Push-pull wire (260) is disposed near the open tops of the "V" shapes of notches (244). Thus, when push-pull wire (260) is pulled proximally, flex section (240) transitions to a deflected configuration, as shown in FIG. 3B. When push-pull wire (260) is then pushed distally, flex section (240) will return toward a straight configuration. A proximal end (234) of push-pull wire (260), shown in FIG. 2, is secured to cam barrel (270) by a retention key (not shown). Proximal end (234) is threaded into one or more lateral openings in a key recess of cam barrel (270); and then the key is inserted into the key recess to retain proximal end (234) in the lateral openings. Translation of cam barrel (270) drives translation of push-pull wire (260), which in turn causes deflection or straightening of flex section (240) as described above.

Cam barrel (270) is movably coupled with rigid shaft member (210) such that cam barrel (270) is slidable longitudinally along rigid shaft member (210); yet cam barrel (270) is prevented from rotating relative to rigid shaft member (210). As shown in FIG. 2, a tab (212) projects laterally and unitarily from a proximal portion of rigid shaft member (210); and is configured to be slidably received within a lateral channel (272) of cam barrel (270). The fit between tab (212) and lateral channel (272) allows cam barrel (270) to slide longitudinally along rigid shaft member (210) while preventing cam barrel (270) from rotating about rigid shaft member (210). Other suitable structures may be used to achieve this relationship between rigid shaft member (210) and cam barrel (270).

A pair of laterally opposed pins (220), shown in FIG. 2, are configured to be fixedly secured in corresponding openings of deflection control knob (280), and are configured to be movably captured in an annular space (214) defined between annular flanges (216, 218) formed at a proximal end of rigid shaft member (210). The relationship between pins (220) and flanges (216, 218) allows deflection control knob (280) to rotate relative to rigid shaft member (210) while preventing deflection control knob (280) from translating relative to rigid shaft member (210). Other suitable structures may be used to achieve this relationship between rigid shaft member (210) and deflection control knob (280).

As noted above, proximal end (264) of push-pull wire (260) is secured to cam barrel (270), such that push-pull wire (260) translates with cam barrel (270) relative to rigid shaft member (210) in response to rotation of deflection control knob (280) relative to rigid shaft member (210). As also noted above, translation of push-pull wire (260) relative to rigid shaft member (210) causes lateral deflection of flex section (240). The operator may thus selectively deflect flex section (240) by rotating deflection control knob (280) relative to rigid shaft member (210).

When deflection control knob (280) is provided in a first rotational position (e.g., a home position), flex section (240) assumes a straight configuration defining a zero deflection angle (or "bend angle") relative to the longitudinal axis of guide shaft assembly (200). In this straight configuration, shaft assembly (200) is suitably configured to guide guidewire (302) and dilation catheter (400) into a first anatomical passageway, such as the sphenoid sinus ostium. When deflection control knob (280) is rotated to a second rotational position, flex section (240) may assume a first deflected (or "bent") configuration defining a first deflection angle relative to the longitudinal axis selected to facilitate access to a second anatomical passageway, such as the Eustachian tube. By way of example only, this first deflection angle may be from approximately 50 degrees to approximately 60 degrees, or more particularly at approximately 55 degrees.

When deflection control knob (280) is further rotated to a third rotational position, flex section (240) may assume a second deflected configuration defining a second deflection angle selected to facilitate access to a third anatomical passageway, such as the frontal recess or frontal sinus ostium. By way of example only, this second deflection angle may be from approximately 65 degrees to approximately 70 degrees, or more particularly at approximately 70 degrees. When deflection control knob (280) is further rotated to fourth rotational position, flex section (240) may assume a third deflected configuration defining a third deflection angle selected to facilitate access to a fourth anatomical passageway, such as the maxillary sinus ostium. By way of example only, this third deflection angle may be from approximately 105 degrees to approximately 115 degrees, or more particularly at approximately 110 degrees.

Cam barrel (270) may be configured to lock in place rotationally such that once the operator achieves a desired deflection angle for flex section (240) using deflection control knob (280), flex section (240) may maintain the selected angle until the operator again rotates knob (280). Since guidewire (302) and dilation catheter (402) are slidably disposed within shaft assembly (200), guidewire (302) and dilation catheter (402) will exit the distal end of shaft assembly (200) at whatever deflection angle the operator has selected. In view of the foregoing, an operator may readily achieve various exit angles for guidewire (302) and dilation catheter (402) by rotating deflection control knob (280) relative to rigid shaft member (210). The operator may thus readily dilate various anatomical passageways without having to exchange instruments; and without having to replace pieces of instrument (10).

In addition to enabling deflection of shaft assembly (200) via flex section (240) and deflection control knob (280), it may be further desirable to enable rotation of shaft assembly (200) about its longitudinal axis, to further facilitate access to various anatomical passageways of a patient. In that regard, instrument (10) of the present example further includes a shaft rotation control knob (290) provided on an upper side of handle assembly (100) and which is selectively rotatable to thereby rotate shaft assembly (200) relative to handle assembly (100). In the present version, shaft rotation control knob (290) is oriented such that its rotational axis is perpendicular to the longitudinal axis of shaft assembly (200). In use, an operator may rotate rotation control knob (290) in first and second directions to thereby effect rotation of shaft assembly (200) in corresponding first and second directions about its longitudinal axis. Rotation control knob (290) is suitably positioned on handle assembly (100) such that the operator may rotate knob (290) using the thumb of the same hand that is grasping handle assembly (100).

The various components of dilation instrument (10), including those shown but not described in detail herein, may be configured and operable in accordance with the teachings of U.S. patent application Ser. No. 16/032,471, entitled "Adjustable Instrument for Dilation of Anatomical Passageway," filed on Jul. 11, 2018, issued as U.S. Pat. No. 10,874,839 on Dec. 29, 2020; and/or U.S. patent application Ser. No. 16/032,489, entitled "Adjustable Instrument for Dilation of Anatomical Passageway," filed on Jul. 11, 2018, issued as U.S. Pat. No. 11,027,105 on Jun. 8, 2021, the disclosures of these references being incorporated by reference herein. Other variations of the features and functionalities described herein will be apparent to those skilled in the art in view of the teachings herein.

II. EXEMPLARY FIBER WIRE HAVING TWISTED FIBER BUNDLE CORE AND FLEXIBLE POLYMER JACKET

By way of example only, some versions of push-pull wire may be formed of steel or nitinol. In some instances, it may be desirable to substitute push-pull wire (260) of dilation instrument (10) with a pull-only wire that has greater flexibility and thus a smaller operating envelope within shaft assembly (200) as compared to steel or nitinol versions of push-pull wire (260). FIGS. 4-8B, described below, show an exemplary version of such a pull wire in the form of fiber wire (500), and an exemplary system (600) and associated method for manufacturing fiber wire (500). While fiber wire (500) is disclosed herein in the context of deflecting shaft assembly (200) of dilation instrument (10), it will be appreciated that fiber wire (500) may be employed for various other uses within dilation instrument (10) and other types of medical devices, as well as in various other applications beyond the medical device industry.

A. Overview of Fiber Wire

Figure 4:
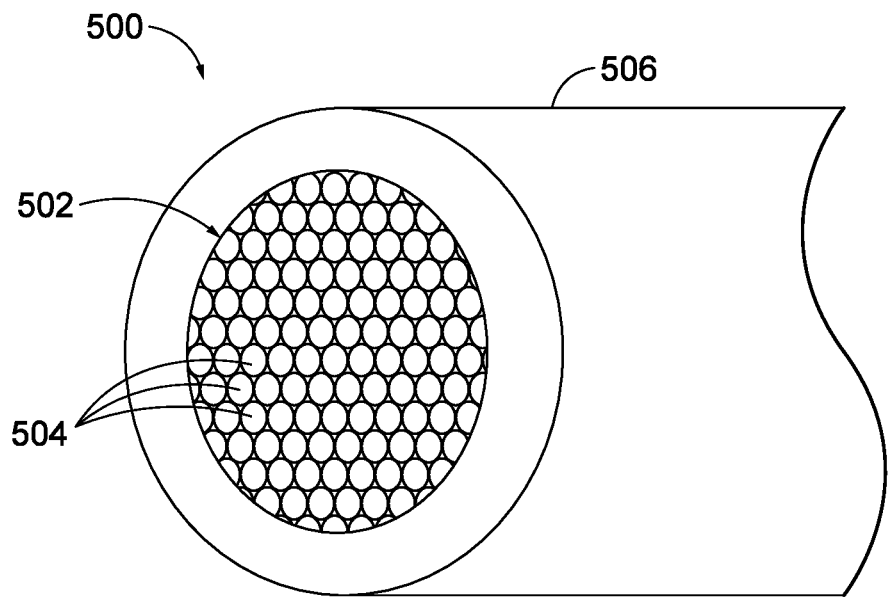
FIG. 4 depicts a perspective end view of an exemplary fiber wire suitable for use as an alternative pull wire in the dilation instrument of FIG. 1A.
Figure 5:
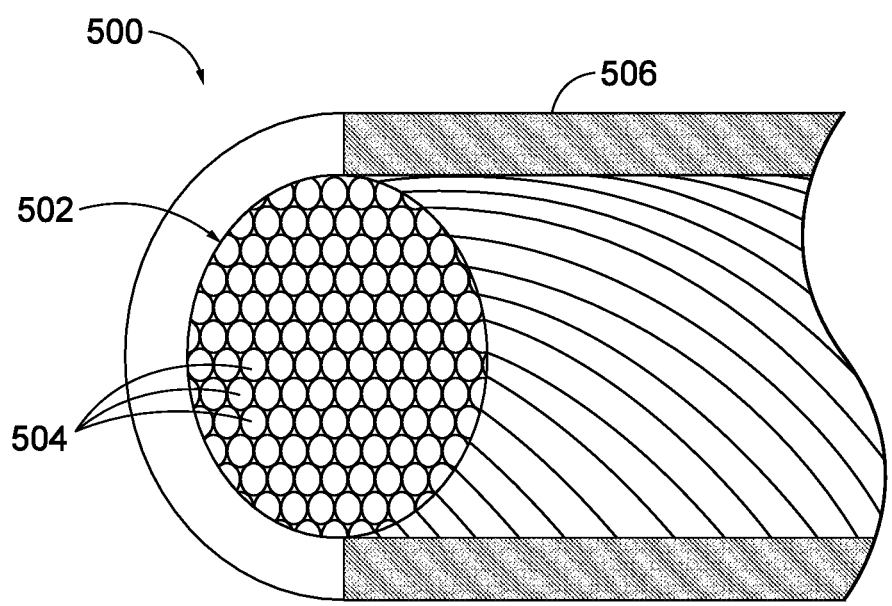
FIG. 5 depicts a perspective end view of the fiber wire of FIG. 4, showing an outer polymer jacket of the fiber wire in cross-section to review details of a fiber bundle core.

As shown in FIGS. 4 and 5, fiber wire (500) includes an inner core defined by a fiber bundle (502) that comprises a plurality of continuous fiber filaments (504), and a flexible polymer jacket (506) that encapsulates fiber bundle (502). As shown in FIG. 5, and as described in greater detail below, fiber bundle (502) is twisted about its longitudinal axis such that each fiber filament (504) extends helically about the longitudinal axis, thus providing fiber bundle (502) with a rope-like configuration. Providing fiber bundle (502) with such a twist renders fiber filaments (504) non-directional and non-biased in lateral directions relative to the longitudinal axis, thereby promoting optimum flexibility of fiber wire (500) in lateral directions relative to the longitudinal axis.

Fiber filaments (504) are continuous linear strands of synthetic material. In some versions, fiber filaments (504) may be formed of a para-aramid material such as Kevlar® or another material having properties similar to Kevlar®. Outer jacket (506) of the present example is formed of a flexible and lubricous material, which may include thermoplastics such as nylon, and is applied to fiber bundle (502) as a continuous molten coating and is then permitted to cool. The material selected for outer jacket (506) may also be bio-compatible and thus safe for direct contact with a patient during a medical procedure, and furthermore capable of withstanding repeated sterilization procedures for bio-burden reduction following use in a medical procedure.

Fiber wire (500) may be formed with a circular cross-sectional shape along its length, as shown in the present version, or with various other round cross-sectional shapes, such as oval. In other versions, fiber wire (500) may be formed with a polygon cross-sectional shape along its length, such as square or elongate rectangular such that fiber wire (500) is shaped as a flat ribbon. Additionally, in various examples, fiber wire (500) may be formed with a maximum cross-sectional width (e.g., diameter) in the range of approximately 0.010 inches to approximately 0.0180 inches.

In some examples, a radial wall thickness of polymer jacket (506) may be in the range of approximately 0.0005 inches to approximately 0.005 inches.

Advantageously, the construction of fiber wire (500) described above exhibits enhanced flexibility and a lower coefficient of friction along its outer surface relative to conventional, uncoated actuating wires employed in dilation instruments, such as push-pull wire (260) described above. In particular, the composition and construction of fiber wire (500) provides it with enhanced flexibility relative to conventional wires comprised of metal, such as stainless steel or nickel-titanium (or "nitinol"), or otherwise comprised of a single, directional filament (or "monofilament"). As a result, fiber wire (500) is capable of being routed around various structures and bends within an operational space, such as within shaft assembly (200), without exhibiting a large catenary typical of conventional wire constructions. As described above, polymer jacket (506) provides a flexible, lubricous, and bio-compatible outer surface, while encapsulating fiber bundle (502) to prevent breakage of individual fiber filaments (504) during use.

As described above, fiber wire (500) may be employed as a substitute for push-pull wire (260) in dilation instrument (10). In particular, a distal end of fiber wire (500) may be coupled with distal end (232) of flexible shaft member (230), distal to flex section (240), and a proximal end of fiber wire (500) may be operatively coupled with deflection control knob (280) via cam barrel (270) or another suitable intervening component. In some versions, the proximal and distal ends of fiber wire (500) may be coupled to respective components of dilation instrument (10) without crimping or otherwise compressing a portion of fiber wire (500) against a coupling structure to thereby avoid damaging fiber wire (500).

As indicated above, fiber wire (500) may be implemented within dilation instrument (10) as a pull-only wire, rather than a push-pull wire. Accordingly, in some versions, shaft assembly (200) of instrument (10) may further include a resilient member (not shown) configured to bias flex section (240) toward a straight configuration, such that proximal translation (or "pulling") of fiber wire (500) via actuation of deflection control knob (280) causes distal flexible shaft member (230) to deflect laterally relative to proximal rigid shaft member (210). In other versions, such a resilient member may be omitted, and dilation instrument (10) may be provided with first and second fiber wires (500), each coupled to and routed along a respective side of the interior of shaft assembly (200). In such versions, the first fiber wire (500) may be actuated proximally to deflect distal flexible shaft portion (230) in a first lateral direction, and the second fiber wire (500) may be actuated proximally to deflect distal flexible shaft portion (230) in an opposite second lateral direction.

It will be appreciated that fiber wire (500) may be employed in a variety of other applications beyond medical devices in which there is a need for a flexible tensile member having a small operational envelope and the other desirable characteristics of fiber wire (500) described above.

B. Exemplary System and Method for Making Fiber Wire

Figure 6:
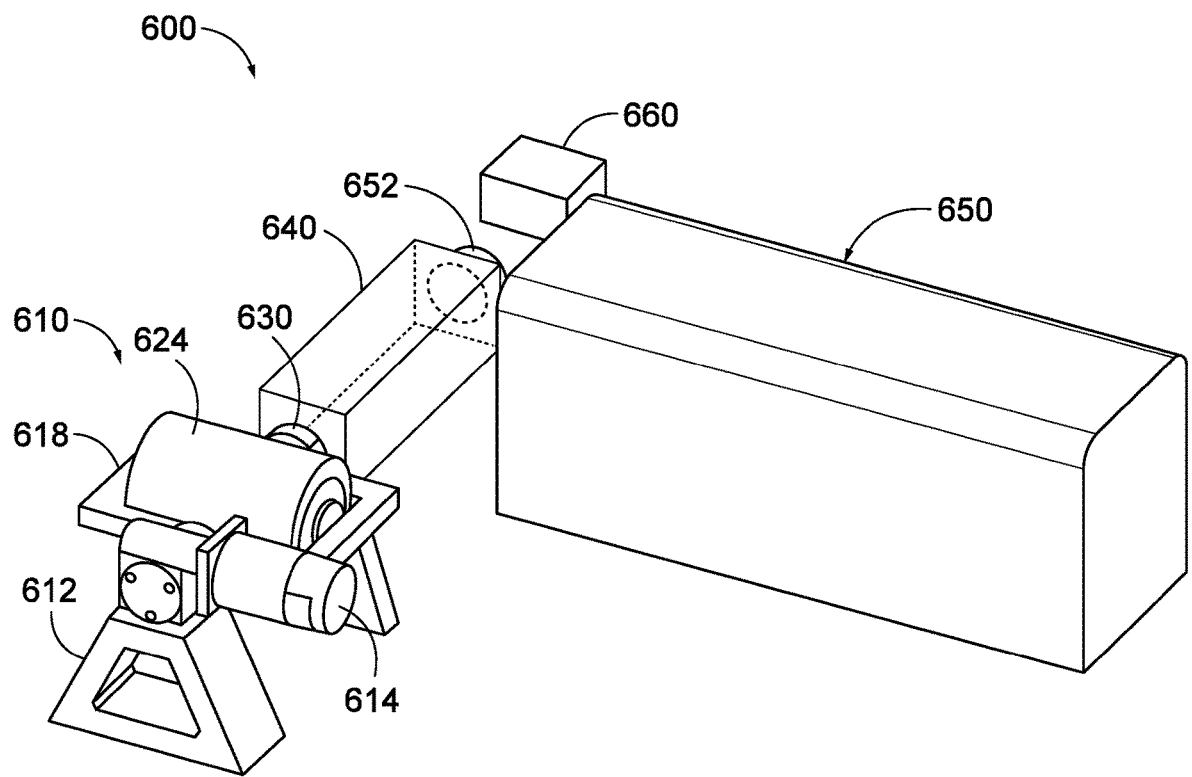
FIG. 6 depicts a schematic perspective view of an exemplary system for manufacturing the fiber wire of FIG. 4.
Figure 7:
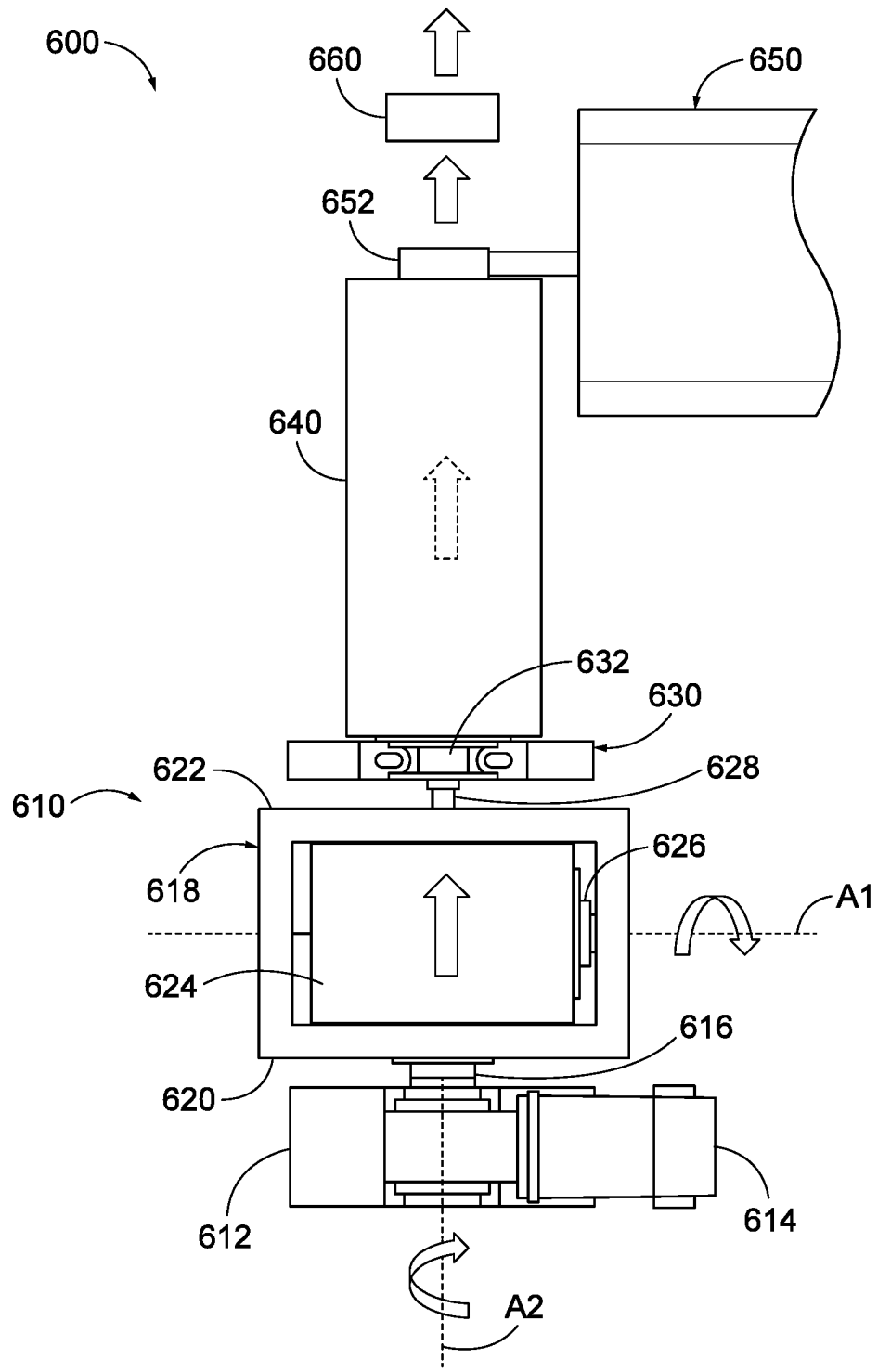
FIG. 7 depicts a schematic top plan view of the system of FIG. 6.

FIGS. 6 and 7 show an exemplary system (600) for manufacturing fiber wire (500) described above. As shown schematically, system (600) of the present version generally includes an unwind apparatus (610), a heat source in the form of a tunnel oven (640) positioned downstream at an output end of unwind apparatus (610), an extruder (650) positioned further downstream at an output end of tunnel oven (640), and a cutting device (660) positioned further downstream at an output end of extruder (650).

Unwind apparatus (610) of the present example includes a base structure in the form of a stand (612) with a motor unit (614) at an upper end thereof, a support frame (618) that rotatably supports a spool (624) of fiber bundle (502), and a fiber guide structure (630). As shown best in FIG. 7, support frame (618) of the present example has a rectangular shape defining a first elongate frame side (620) and a second elongate frame side (622). Spool (624) is mounted to a rotatable spool shaft (626) that extends parallel between first and second elongate frame sides (620, 622), and which is configured to enable spool (624) to rotate relative to support frame (618) about a first rotational axis (A1) to thereby unwind and feed fiber bundle (502) from spool (624) toward fiber guide structure (630). Spool shaft (626) of the present example incorporates a variable tension brake operable to regulate a rotational speed of spool (624) relative to support frame (618). First elongate frame side (620) of support frame (618) is coupled with a drive shaft (616) of motor unit (614), and second elongate frame side (622) is rotatably coupled with fiber guide structure (630) via a support shaft (628). Motor unit (614) of stand (612) is operable to rotate support frame (618) and spool (624) relative to stand (612) and fiber guide structure (630) about a second rotational axis (A2) that extends perpendicular to first rotational axis (A1), while spool rotates relative to support frame (618) about first rotational axis (A1).

Fiber guide structure (630) of the present example includes a guide mechanism (632) operable to receive fiber bundle (502) as fiber bundle (502) is unwound from spool (624) when spool (624) rotates about first rotational axis (A1). Guide mechanism (632) may be in the form of a pair of rollers, for example. In some versions, guide mechanism (632) may be powered to actively draw fiber bundle (502) from spool (624), such that spool (624) freely rotates about first rotational axis (A1) in response to activation of guide mechanism (632). In other versions, spool shaft (626) may be powered to drive rotation of spool (624) about first rotational axis (A1). In either case, guide mechanism (632) is rotationally fixed relative to support frame (618) about second rotational axis (A2), such that guide mechanism (632) is configured to maintain a rotational orientation of fiber bundle (502) about second rotational axis (A2) as fiber bundle (502) is received through guide mechanism (632).

Figure 8A:
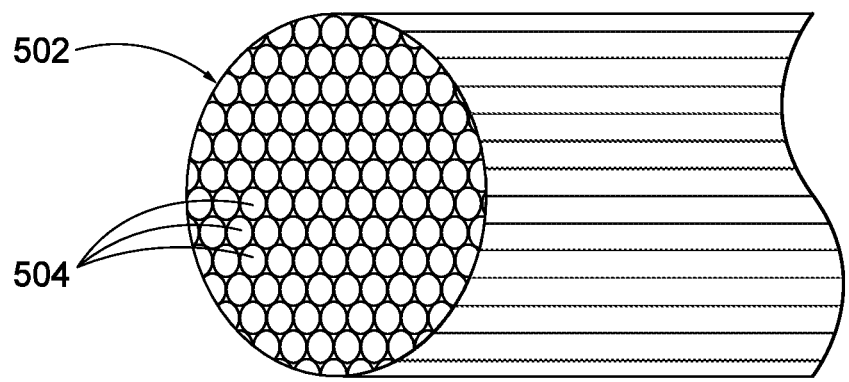
FIG. 8A depicts a perspective end view of a fiber bundle used to create the fiber wire of FIG. 4, showing the fiber bundle before being twisted by components of the system of FIG. 6.
Figure 8B:
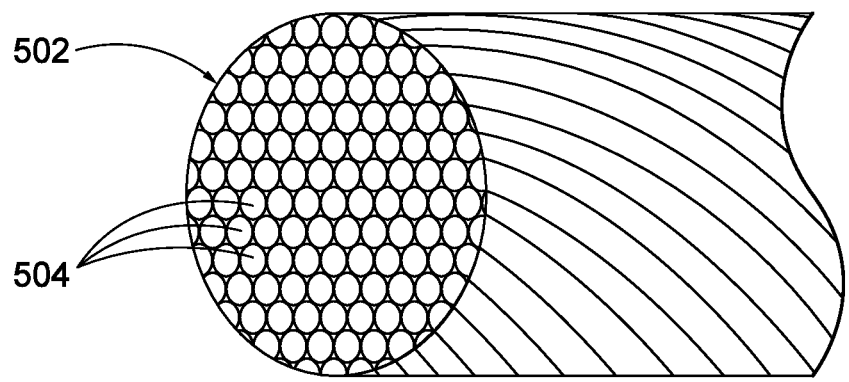
FIG. 8B depicts a perspective end view of the fiber bundle of FIG. 8A, showing the fiber bundle after being twisted by components of the system of FIG. 6.

Accordingly, guide mechanism (632) is configured to cooperate with stand (612) and support frame (618) to provide fiber bundle (502) with a twisted configuration about its own longitudinal axis as fiber bundle (502) is unwound from spool (624). FIG. 8A shows fiber bundle (502) in an untwisted configuration before fiber bundle (502) is unwound from spool (624). In this configuration, each fiber filament (504) of fiber bundle (502) extends parallel to a longitudinal axis of fiber bundle (502), without wrapping around the longitudinal axis. FIG. 8B shows fiber bundle (502) in a twisted configuration that results from fiber bundle (502) being twisted about its own longitudinal axis in response to rotation of spool (624) about second rotational axis (A2), as spool (624) is unwound about first rotational axis (A1). In this twisted configuration, each fiber filament (504) of fiber bundle (502) extends helically about the longitudinal axis of fiber bundle (502). As described above, this twisted configuration provides fiber wire (500) with enhanced flexibility in various lateral directions relative to the longitudinal axis.

After the twisted fiber bundle (502) is received through guide mechanism (632) of fiber guide structure (630), it is then directed through tunnel oven (640). Tunnel oven (640) is configured to pre-heat the twisted fiber bundle (502) in preparation for application of a molten polymer coating applied by extruder (650). Upon exiting tunnel oven (640), twisted fiber bundle (502) is directed through a die (652) of extruder (650). Extrusion die (652) applies a continuous coating of molten polymer, such as nylon or various other suitable thermoplastics. Additionally, extrusion die (652) may be suitably shaped to provide the coated fiber bundle (502) with a desired cross-sectional shape, such as any of the exemplary shapes described above. After exiting extrusion die (652), the molten polymer coating applied to twisted fiber bundle (502) cools to define outer jacket (506) described above. Extrusion die (652) may be configured to apply any desired amount of molten polymer to fiber bundle (502) as it passes therethrough to provide jacket (506) with a selected wall thickness upon cooling. After exiting die (652), the formed fiber wire (500) is directed through cutting device (660), which cuts fiber wire (500) into sections of predetermined length. The resulting cut section of fiber wire (500) has a core of twisted fiber bundle (502) and a continuous outer polymer jacket (506), the characteristics of which are described in greater detail above.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of making a fiber wire having a fiber bundle core and a polymer jacket, the method comprising: (a) rotating a spool of fiber bundle about a first rotational axis to progressively unwind the fiber bundle from the spool, wherein the fiber bundle comprises a plurality of continuous synthetic fiber filaments; (b) while rotating the spool about the first rotational axis, simultaneously rotating the spool about a second rotational axis to thereby twist the unwound fiber bundle about a longitudinal axis of the unwound fiber bundle; (c) coating the twisted fiber bundle with a molten polymer; and (d) permitting the molten polymer to cool to define a flexible outer jacket that encapsulates the twisted fiber bundle.

Example 2

The method of Example 1, wherein the spool is rotatably mounted to a support frame about the first rotational axis, wherein the support frame is rotatably mounted to a base structure about the second rotational axis.

Example 3

The method of Example 2, wherein rotating the spool about the first rotational axis comprises rotating the spool relative to the support frame, wherein rotating the spool about the second rotational axis comprises rotating the support frame relative to the base structure.

Example 4

The method of any of the preceding Examples, wherein the first rotational axis is perpendicular to the second rotational axis.

Example 5

The method of any of the preceding Examples, wherein coating the twisted fiber bundle with the molten polymer comprises directing the twisted fiber bundle through an extrusion die.

Example 6

The method of any of the preceding Examples, further comprising providing the coated fiber bundle with an outer diameter in the range of 0.0120 inches to 0.0180 inches.

Example 7

The method of any of the preceding Examples, further comprising heating the twisted fiber bundle before coating the twisted fiber bundle.

Example 8

The method of any of the preceding Examples, wherein heating the twisted fiber bundle comprises directing the twisted fiber bundle through a tunnel oven.

Example 9

The method of any of the preceding Examples, further comprising providing the coated fiber bundle with a round cross-sectional shape.

Example 10

The method of any of the preceding Examples, further comprising cutting the coated fiber bundle into predetermined lengths.

Example 11

The method of any of the preceding Examples, wherein the flexible outer jacket is continuous along a selected length of the twisted fiber bundle.

Example 12

The method of any of the preceding Examples, wherein the fiber filaments comprise a synthetic material.

Example 13

The method of any of the preceding Examples, wherein the fiber filaments comprise a para-aramid material.

Example 14

The method of any of the preceding Examples, wherein the polymer comprises a thermoplastic.

Example 15

The method of any of the preceding Examples, wherein the polymer comprises nylon.

Example 16

A system for making a fiber wire having a fiber bundle core and a polymer jacket, comprising: (a) a spool of fiber bundle, wherein the fiber bundle comprises a plurality of continuous synthetic fiber filaments; (b) a support frame, wherein the support frame rotatably supports the spool about a first rotational axis; (c) a base structure, wherein the base structure rotatably supports the support frame about a second rotational axis, wherein the support frame and the base structure are operable to cooperate to rotate the spool about the first and second axes simultaneously to thereby unwind fiber bundle from the spool and simultaneously twist the unwound fiber bundle about a longitudinal axis of the unwound fiber bundle; and (d) a die positioned downstream of the spool, wherein the die is operable to apply a molten polymer coating to the twisted fiber bundle, wherein the molten polymer coating is configured to cool to define a jacket that encapsulates the twisted fiber bundle.

Example 17

The system of Example 16, further comprising a heat source positioned between the spool and the die, wherein the heat source is operable to heat the twisted fiber bundle before being coated by the die.

Example 18

An apparatus, comprising: (a) a body; (b) a shaft assembly extending distally from the body, wherein the shaft assembly comprises: (i) a rigid proximal portion, and (ii) a flexible distal portion; and (c) a deflection actuation assembly comprising: (i) an actuator, and (ii) a wire having a proximal end coupled with the actuator and a distal end coupled with the shaft assembly, wherein the wire is flexible about its longitudinal axis and is configured to deflect the flexible distal portion relative to the rigid proximal portion in response to movement of the actuator, wherein the wire comprises: (A) a fiber bundle having a plurality of fiber filaments, wherein the fiber filaments are arranged helically about a longitudinal axis of the wire, and (B) a polymer jacket that encapsulates the fiber bundle.

Example 19

The apparatus of Example 18, wherein the fiber filaments comprise a para-aramid material, wherein the polymer jacket comprises a thermoplastic material.

Example 20

The apparatus of any of Examples 18 through 19, further comprising a dilation catheter slidable relative to the shaft assembly, wherein the dilation catheter includes an expandable dilator.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of making a fiber wire having a fiber bundle core and a polymer jacket, the method comprising:
   (a) rotating a single spool of fiber bundle about a first rotational axis to progressively unwind the fiber bundle from the single spool, wherein the fiber bundle comprises a plurality of continuous synthetic fiber filaments;
   (b) while rotating the single spool about the first rotational axis, simultaneously rotating the single spool about a second rotational axis to thereby twist the unwound fiber bundle about a longitudinal axis of the unwound fiber bundle;
   (c) coating the twisted fiber bundle with a molten polymer; and
   (d) permitting the molten polymer to cool to define a flexible outer jacket that encapsulates the twisted fiber bundle.

2. The method of claim 1, wherein the single spool is rotatably mounted to a support frame about the first rotational axis, wherein the support frame is rotatably mounted to a base structure about the second rotational axis.

3. The method of claim 2, wherein rotating the single spool about the first rotational axis comprises rotating the single spool relative to the support frame, wherein rotating the single spool about the second rotational axis comprises rotating the support frame relative to the base structure.

4. The method of claim 1, wherein the first rotational axis is perpendicular to the second rotational axis.

5. The method of claim 1, wherein coating the twisted fiber bundle with the molten polymer comprises directing the twisted fiber bundle through an extrusion die.

6. The method of claim 1, further comprising providing the coated fiber bundle with an outer diameter in the range of 0.0120 inches to 0.0180 inches.

7. The method of claim 1, further comprising heating the twisted fiber bundle before coating the twisted fiber bundle.

8. The method of claim 7, wherein heating the twisted fiber bundle comprises directing the twisted fiber bundle through a tunnel oven.

9. The method of claim 1, further comprising providing the coated fiber bundle with a round cross-sectional shape.

10. The method of claim 1, further comprising cutting the coated fiber bundle into predetermined lengths.

11. The method of claim 1, wherein the flexible outer jacket is continuous along a selected length of the twisted fiber bundle.

12. The method of claim 1, wherein the fiber filaments comprise a synthetic material.

13. The method of claim 1, wherein the fiber filaments comprise a para-aramid material.

14. The method of claim 1, wherein the polymer comprises a thermoplastic.

15. The method of claim 1, wherein the polymer comprises nylon.

16. A system for making a fiber wire having a fiber bundle core and a polymer jacket, comprising:
   (a) a single spool of fiber bundle, wherein the fiber bundle comprises a plurality of continuous synthetic fiber filaments;
   (b) a support frame, wherein the support frame rotatably supports the single spool about a first rotational axis;
   (c) a base structure, wherein the base structure rotatably supports the support frame about a second rotational axis, wherein the support frame and the base structure are operable to cooperate to rotate the single spool about the first and second axes simultaneously to thereby unwind fiber bundle from the single spool and simultaneously twist the unwound fiber bundle about a longitudinal axis of the unwound fiber bundle; and
   (d) a die positioned downstream of the single spool, wherein the die is operable to apply a molten polymer coating to the twisted fiber bundle, wherein the molten polymer coating is configured to cool to define a jacket that encapsulates the twisted fiber bundle.

17. The system of claim 16, further comprising a heat source positioned between the single spool and the die, wherein the heat source is operable to heat the twisted fiber bundle before being coated by the die.

18. A method of making a fiber wire having a fiber bundle core and a polymer jacket with an apparatus including a spool of fiber bundle, a spool shaft, a support frame, and a base structure, wherein the spool of fiber bundle is mounted to the spool shaft, wherein the support frame extends distally from a first frame end to a second frame end along a first rotational axis, wherein the spool shaft is rotatably mounted within the support frame along a second rotational axis transverse to the first rotational axis, wherein the base structure rotatably supports the support frame, the method comprising:
   (a) rotating the spool of fiber bundle relative to the support frame about the second rotational axis to progressively unwind the fiber bundle from the spool, thereby creating an unwound fiber bundle, wherein the fiber bundle comprises a plurality of continuous synthetic fiber filaments;
   (b) while rotating the spool about the first rotational axis, simultaneously rotating the support frame about the second rotational axis to thereby twist the unwound fiber bundle about a longitudinal axis of the unwound fiber bundle;
   (c) heating the twisted fiber bundle before coating the twisted fiber bundle; and
   (c) coating the twisted fiber bundle with a molten polymer.

19. The method of claim 18, wherein heating the twisted fiber bundle comprises directing the twisted fiber bundle through a tunnel oven.

20. The method of claim 19, wherein the coated fiber bundle has an outer diameter in the range of 0.0120 inches to 0.0180 inches.

\* \* \* \* \*